United States Patent [19]

James

[11] 4,335,137
[45] Jun. 15, 1982

[54] HALOETHENYLTHIENYLETHANONES FOR SYSTEMIC NEMATODE CONTROL

[75] Inventor: Donald R. James, Lockport, N.Y.

[73] Assignee: FMC Corporation, Philadelphia, Pa.

[21] Appl. No.: 130,937

[22] Filed: Mar. 17, 1980

[51] Int. Cl.³ .......................................... A01N 43/02
[52] U.S. Cl. .................................................... 424/275
[58] Field of Search ........................................ 424/275

[56] References Cited

U.S. PATENT DOCUMENTS 2,651,579  9/1953  Plump .................................. 424/275
3,904,760  9/1975  Ariyan et al. ....................... 424/275

FOREIGN PATENT DOCUMENTS 2810262  9/1978  Fed. Rep. of Germany .

OTHER PUBLICATIONS

Handele, Synthese, Spectra En Nematicide Activiteit Van 1,2-Dithienylethenen En 1-Fenyl-2-Thienylethenen, Thesis, University of Utrecht, 1971, Capt. 5.

*Primary Examiner*—Douglas W. Robinson
*Attorney, Agent, or Firm*—Robert L. Andersen; H. Robinson Ertelt

[57] ABSTRACT

A method is disclosed for systemic control of nematodes in agricultural crops which comprises applying to the above ground portions of the plants comprising said agricultural crop of a nematicidal amount of a compound of the formula

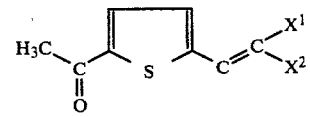

wherein $X^1$ and $X^2$ are each halogen atoms selected from bromine, chlorine and fluorine, the same or different. Preparation, formulation and nematicidal utility for the compounds are described and exemplified.

6 Claims, No Drawings

HALOETHENYLTHIENYLETHANONES FOR SYSTEMIC NEMATODE CONTROL

The present invention relates to a method and composition for systemic control of nematodes. More particularly, the invention relates to dihaloethenylthienylethanones for systemic control of nematodes in agricultural crops.

Dihaloethenylthiophenes are known to be useful as intermediates for the preparation of pharmaceuticals. German Offenlegungsschrift No. 2810262, published Sept. 28, 1978, generically describes compounds useful for that purpose and specifically exemplifies 2-(2,2-dichloroethenyl)thiophene. Certain ethenylthiophenes have been reported by Handele to have nematicidal activity, for example, 1,2-di(2-thienyl)-ethenes and 1-phenyl-2-thienyl ethenes. See M. J. Handele, *SYNTHESE, SPECTRA EN NEMATICIDE ACTIVITEIT VAN 1,2-DITHIENYLETHENEN EN 1-FENYL-2-THIENYLETHENEN*, Thesis, University of Utrecht, 1971. Certain dihaloethenylnitrofurans are also said to have nematicidal activity. See, for example, U.S. Pat. No. 4,024,161, issued May 17, 1977.

The prior copending application of Donald R. James, U.S. Ser. No. 111,506, filed Jan. 11, 1980, describes a genus of haloethenylthiophenes in which the thiophene ring is unsubstituted or substituted with halogen, lower alkyl, or nitro. Two compounds within the scope of that application, both having a fully substituted ethenyl group, were shown to have some systemic nematicidal activity.

There are two known types of systemic activity, upward systemic activity in which a chemical is applied to the soil or plant roots and is transported upwardly to the above ground portions of the plant, and downward systemic activity in which a chemical applied to the above-ground portions of a plant is transported downwardly into the roots and/or surrounding soil where its activity takes place. In this application the word "systemic" refers to the presence of the latter (downward) type of systemic activity, but not necessarily to the exclusion of upward systemic transportation.

In accordance with the present invention there is provided a method and composition for systemic control of nematodes in agricultural crops. The method aspect of the invention comprises applying to the above-ground portions of an agricultural plant a nematicidally effective amount of the compound 5-(2,2-dihaloethenyl)-2-thienylethanone; that is, a compound of the formula

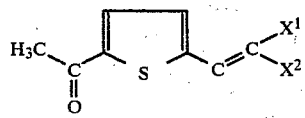

wherein each X, the same or different, is a halogen atom, suitably bromine, chlorine or fluorine. The preferred compounds of this invention are those in which each X is bromine or chlorine, most preferably those in which both $X^1$ and $X^2$ are the same.

The nematicides of this invention, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of a toxicant may affect the activity of the material. The present compounds may be applied, for example, as powders or liquids, the choice of application varying, of course, with the nematode species and environmental factors present at the particular locus of infestation. Thus, the compounds may be formulated as granules, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these nematicides, are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp < 100° C.) are suitably formulated in the concentration range of 5 to 50% by weight, usually from 10 to 30%; high melting solids (mp > 100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Microencapsulated or other controlled release formulations may also be used with hematicides of this invention for control of nematodes.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

Flowables are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the nematicide in use dilution is normally in the range of about 2% to about 0.1%. Many variations of spraying, dusting, and controlled or slow release compositions in the art may be used by substituting or adding a compound of this invention into compositions known or apparent to the art.

Nematicidal compositions may be formulated and applied with other suitable active ingredients, including other nematicides, insecticides, acaricides, fungicides, plant regulators, herbicides, fertilizers, etc.

In applying the foregoing chemicals, an effective nematicidal amount must be applied. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare. Trees and vines for example may require at least 5 kg/hectare whereas annuals such as corn may require considerably lower rates of application, for example 1 to 5 kg/hectare.

The compounds of this invention are prepared by reacting 2-(2,2-dichloroethenylthiophene) with acetyl chloride and aluminum chloride as illustrated in the following example.

EXAMPLE 1

Synthesis of 5-(2,2-dichloroethenyl)-2-thienylethanone

Step A

Synthesis of 2,2,2-trichloro-1-(2-thienyl)-ethanol as an intermediate Under a dry argon atmosphere a Grignard reagent was prepared by combining 13.1 g (0.54 mole) of magnesium turnings with 86.4 g (0.53 mole) of 2-bromothiophene in dry diethyl ether. The Grignard reagent was stirred and cooled to 5° C., and 77.8 g (0.53 mole) of chloral was added slowly. The reaction mixture was allowed to stir overnight at room temperature. The reaction mixture was poured into 500 ml of cold water and extracted with three 250 ml portions of ethyl acetate. The combined organic extracts were dried with magnesium sulfate and filtered. The solvent was removed from the filtrate under reduced pressure to yield a liquid. The liquid was distilled under reduced pressure to give 67.2 g of 2,2,2-trichloro-1-(2-thienyl)ethanol; bp 113°–115° C./19.95 pa. The ir spectrum was consistent with the proposed structure.

Step B

Synthesis of 2-(2,2-dichloroethenyl)thiophene as an intermediate

To a stirred mixture of 36.3 g (0.555 mole) of zinc in 250 ml of glacial acetic acid, 64.2 g (0.277 mole) of 2,2,2-trichloro-1-(2-thienyl)ethanol was added dropwise. The reaction mixture was stirred at room temperature overnight. The reaction mixture was poured into 600 ml of cold water and the mixture extracted with three 250 ml portions of ethyl acetate. The combined organic extracts were dried with magnesium sulfate and filtered. The solvent was removed from the filtrate to give a liquid which was distilled under reduced pressure to give 2-(2,2-dichloroethenyl)thiophene; bp 60°–68° C./266 pa. The ir spectrum was consistent with the proposed structure.

Step C

Synthesis of 5-(2,2-dichloroethenyl)-2-thienylethanone Under a dry argon atmosphere, a stirred solution of 3.0 g (0.017 mole) of 2-(2,2-dichlorothenyl)thiophene and 1.33 g (0.017 mole) of acetyl chloride in 10 ml of methylene chloride was cooled to −20° C. During a five minute period 2.24 g (0.017 mole) of anhydrous aluminum chloride was added. The reaction mixture was warmed to 10° C., then poured into 250 ml of cold water. The resultant mixture was extracted with two 100 ml portions of diethyl ether. The combined extracts were washed with 30 ml of a dilute sodium carbonate solution, dried with anhydrous sodium sulfate and filtered. The solvent was evaporated to give a brown solid. The solid was dissolved in a small amount of toluene and subjected to column chromatography on 100 g silica gel using n-heptane followed by a solution of 10% ethylacetate in n-heptane as eluant. A white solid was obtained and recrystallized from n-heptane to give 2.5 g of crude product. A sample of the crude product was sublimed at 90° C./7 pa to yield 5-(2,2-dichloroethenyl)-2-thienylethanone; mp 81°–85° C. The nmr and ir spectra were consistent with the proposed structure.

Analysis calc'd for $C_8H_6Cl_2OS$: C 43.45; H 2.74; Cl 32.07; S 14.50; Found: C 43.58; H 2.69; Cl 32.10; S 14.52.

For biological testing the compound of Example 1 was dissolved in acetone and an aqueous acetone solution containing 2 lbs. of active ingredient per 100 gallons was prepared. Twelve four to five week old tomato plants were transplanted into individual three inch pots containing sterilized soil. Four plants were sprayed with the aqueous acetone solution of the compound of Example 1. Another four plants were sprayed with an aqueous solution of 2 lbs. carbofuran* per 100 gals., and the remaining four plants were untreated and used as check plants. One day after the plants were sprayed the soil of two plants from each group of four was inoculated with soil infested with root-knot nematode larvae. Seven days after spraying the soil of the remaining plants was inoculated with the infested soil. Three weeks after spraying the roots of all plants were examined and rated in comparison to the untreated check plants.

*Carbofuran is the common or generic name for the 2,3-dihydro-2,2-dimethyl-7-benzofuranyl methylcarbamate, a commercially available nematicide.

The plants inoculated with the compound of Example 1 one day after spraying showed 50–75% nematode control with no plant injury. The corresponding plants sprayed with carbofuran showed about the same level of control but with slight symptoms of plant toxicity. The plants inoculated with the compound of Example 1 seven days after spraying showed 75–80% control again with no plant injury. The corresponding carbofuran treated plants showed about 75% control, again with slight plant injury.

From this test it would appear that the compound of this invention is equal to or slightly more active than carbofuran as a systemic nematicide, and that it exhibits less plant toxicity at comparable application concentrations.

I claim:

1. A method for systemic control of nematodes which comprises applying to the above-ground portions of an agricultural plant a nematicidally effective amount of a compound of the formula

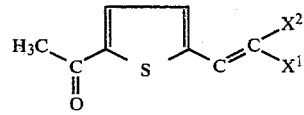

in which $X^1$ and $X^2$ are each halogen selected from bromine, chlorine, and fluorine.

2. The method of claim 1 in which said compound is 5-(2,2-dihaloethenyl)-2-thienylethanone.

3. The method of claim 1 wherein the compound is 5-(2,2-dichloroethenyl)-2-thienylethanone.

4. A nematicidal composition comprising a nematicidally effective amount of a compound of the formula

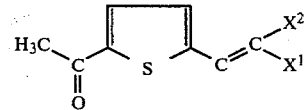

in which $X^1$ and $X^2$ are each halogen selected from the group consisting of bromine, chlorine and fluorine, in admixture with an agriculturally acceptable adjuvant, carrier, or diluent.

5. The composition of claim 4 in which said compound is 5-(2,2-dihaloethenyl)-2-thienylethanone.

6. A nematicidal composition of claim 3 in which said compound is 5-(2,2-dichloroethenyl)-2-thienylethanone.

* * * * *